United States Patent
Hermansson et al.

(10) Patent No.: US 7,351,281 B2
(45) Date of Patent: *Apr. 1, 2008

(54) POWDERED MATERIAL AND CERAMIC MATERIAL MANUFACTURED THEREFROM

(75) Inventors: Leif Hermansson, Länna (SE); Lars Kraft, Uppsala (SE); Håkan Engqvist, Knivsta (SE); Irmeli Hermansson, Uppsala (SE); Nils-Otto Ahnfelt, Uppsala (SE); Gunilla Gomez-Ortega, Uppsala (SE)

(73) Assignee: Doxa Aktiebolag, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/490,628

(22) PCT Filed: Aug. 21, 2002

(86) PCT No.: PCT/SE02/01481

§ 371 (c)(1), (2), (4) Date: Mar. 25, 2004

(87) PCT Pub. No.: WO03/041662

PCT Pub. Date: May 22, 2003

(65) Prior Publication Data

US 2004/0206273 A1 Oct. 21, 2004

(30) Foreign Application Priority Data

Sep. 26, 2001 (SE) .................................... 0103190
Apr. 9, 2002 (SE) .................................... 0201067

(51) Int. Cl.
*C04B 28/06* (2006.01)
*A61K 6/06* (2006.01)

(52) U.S. Cl. .................. 106/692; 106/693; 106/694; 106/695; 106/696; 106/35; 106/814

(58) Field of Classification Search ............ 501/32, 501/125; 252/301.4 R; 106/35, 816, 692, 106/814, 716, 690, 691, 712, 695, 819
See application file for complete search history.

(56) References Cited

U.S. PATENT DOCUMENTS

| | | | | |
|---|---|---|---|---|
| 1,789,197 | A | * | 1/1931 | Seailles et al. ............. 428/409 |
| 4,174,334 | A | * | 11/1979 | Bertenshaw et al. ........ 524/443 |
| 6,107,229 | A | * | 8/2000 | Luck et al. ................. 501/151 |
| 6,280,863 | B1 | | 8/2001 | Frank et al. |
| 6,620,232 | B1 | | 9/2003 | Kraft et al. |

FOREIGN PATENT DOCUMENTS

| | | | |
|---|---|---|---|
| EP | 0559627 | | 9/1993 |
| JP | 51-111828 | * | 10/1976 |
| JP | 53-037488 | | 4/1978 |
| JP | 57-209871 | * | 12/1982 |
| WO | WO 90/11066 | | 10/1990 |
| WO | WO 00/21489 | * | 4/2000 |
| WO | WO 00/21489 A1 | | 4/2000 |

OTHER PUBLICATIONS

English language abstract of JP 57-209871, Dec. 23, 1982.
Database WPI, Week 197646, Derwent Publications Ltd., London, GB, Class C04B, AN 1976-86141X & JP 51111828 A (Matsushita Electric Works Ltd.) Oct. 2, 1976—Abstract.

* cited by examiner

*Primary Examiner*—C. Melissa Koslow
(74) *Attorney, Agent, or Firm*—Birch, Stewart, Kolasch & Birch, LLP

(57) ABSTRACT

Powdered material, the binder phase of which mainly consists of a cement-based system, which powdered material has the capacity following saturation with a liquid reacting with the binder phase to hydrate to a chemically bonded ceramic material, preferably for dental purposes. According to the invention the powdered material has a composition and/or structure suitable for giving the ceramic material translucence in the hydrated state. The invention also relates to the ceramic material produced by hydration of the powdered material.

18 Claims, No Drawings

POWDERED MATERIAL AND CERAMIC MATERIAL MANUFACTURED THEREFROM

TECHNICAL FIELD

The present invention relates to a chemically bonded ceramic material, the binder phase of which consists mainly of a cement-based system, which material is preferably suited to dental purposes. The invention also relates to a powdered material that has the capacity to form said ceramic material when it is saturated with a liquid reacting with the binder phase.

PRIOR ART AND PROBLEMS

The present invention relates to binding agent systems of the cement system type, in particular the system $CaO$—$Al_2O_3$—$(SiO_2)$—$H_2O$. Studies carried out according to the invention and earlier works (SE 463 493, SE 502 987 and SE 514 686) have produced results that indicate great potential for the system for strong and acid-resistant materials such as dental filling material. No other dental filling material existing today meets all the requirements in respect of biocompatibility, aesthetics and function that can be posed by patients and dental service staff.

A description is given below of the practical demands that should generally be made on a dental filling material. Good handling ability with simple applicability in a cavity, moulding that permits good modellability, hardening/solidification that is sufficiently rapid for filling work and provides serviceability directly following a visit to the dentist. Furthermore, high strength and corrosion resistance exceeding that of earlier filling materials, good biocompatibility, radiopacity for X-ray purposes, good aesthetics and safe handling for staff without any allergy-provoking or toxic additives in the material are required. Good long-term attributes as regards dimensional stability are also demanded.

In SE 463 493 it was described how a chemically bonded ceramic material, e.g. for dental purposes, can be caused to exhibit increased strength characteristics in that a powder body consisting of one or more hydraulic binding agents and possible ballast material is compacted at such a high external pressure and at so low a temperature that a well held-together raw compact is obtained without sintering reactions on compacting. The filling density in this raw compact has increased to at least 1.3 times the initial filling density, which is defined as the filling density attained through shaking, vibration and/or light packing of the loose powder into a container. The user of the material prepares the same by saturating the raw compact with a hydration liquid prior to application of the material or in situ in a cavity, e.g. a tooth cavity.

More recently it was shown in SE 502 987 that for cement systems complete hydration (which was regarded as reducing the risk of dimensional changes) can take place if complete soaking and subsequent compaction of the cement system takes place with the aid of a specially designed stopper.

More recently still it has been shown in SE 514 686 that a cement system of the type referred to in SE 463 493 or SE 502 987 can be caused to exhibit dimensionally stable long-term attributes if the material includes one or more expansion-compensating additives.

Materials that are manufactured according to SE 463 493, SE 502 987 or SE 514 686 have certainly proved to satisfy most of the demands that can be made according to the above on dental filling material. However, it has proved to be the case that the aesthetics of the material suffer, in spite of tooth coloring, due to the fact that the material is opaque, which means that the material does not have adequate optical attributes to appear natural. Natural tooth transmits light, especially enamel. The manner in which the light is diffused through the tooth is described as translucent, which is to be differentiated from transparent. A definition of a translucent material reads: "A material that reflects, transmits and absorbs light. Objects cannot be seen clearly through the material when the material is placed between the object and the observer." (Lemire, Burk, Color in dentistry, J. M. Ney Company (1975)). One method of measuring translucence is to determine the ratio between the quantity of reflected light with a white background and with a black background (ISO 9917). A material is described as translucent if it has opacity of between 35 and 90%, as opaque above 90% and transparent below 35%. Natural dentine has an opacity of approx. 70%, while natural enamel has an opacity of around 35%. The ability of a filling material to imitate the appearance of the natural tooth depends to a large extent on the material being translucent.

In the abstract to JP 57209871 it is stated that translucence can be attained in a material of Portland cement and water glass.

In JP 51111828, a method is described for the production of $3CaO.Al_2O_3.6H_2O$. In the method, the raw materials for the binder phase are mixed with a surplus of water for 1-20 hours, with gradual heating from room temperature to 100° C. It is stated that hydrated calcium aluminate in the form of $3CaO.Al_2O_3.6H_2O$ is formed thereby. This hydrated calcium aluminate is heated to between room temperature and 100° C. and compressed at the same time at 50-800 MPa for 10-60 minutes, possibly following the addition of further water, to form a ceramic that is then dried at 60-250° C. without the water of crystallization being evaporated. In the method described in JP 51111828, the mechanical compression of already hydrated material is thus executed. However, it is said that the ceramic formed exhibits translucence.

A related problem is that of achieving radiopacity at the same time as translucence, the former being required in a filling material in order for it to be clearly distinguishable from natural tooth and the onset of decay respectively in X-rays. The problem is due to the fact that the X-ray contrast aids that are common nowadays, e.g. $ZrO_2$ and $SnO_2$, interfere with the translucence.

Yet another problem is that of achieving other optical effects (luminescence) in the material at the same time as translucence and radiopacity, which optical effects imitate optical effects of natural tooth. A natural tooth fluoresces, for example, when illuminated by light containing UV light, e.g. daylight. Fluorescence means that a material has the capacity to absorb light of a short wavelength (high energy) and then emit light of another, longer wavelength (lower energy). This property makes the tooth come to life and be seen as whiter in daylight than in room lighting (which does not contain UV). According to Monsénégo, Burdairon, Clerjaud, Fluorescence of dental porcelain, The journal of prosthetic dentistry, Vol. 69, No. 1, January 1993, natural tooth has its emission maximum at a light wavelength of 450 nm, which corresponds to blue light.

Fluorescence in combination with translucence in teeth makes the fluorescent light appear to come from inside the material. It is desirable for a material intended for fillings to combine translucence and fluorescence for it to be seen like natural tooth. As stated, it is also desirable for these attributes to be combined with the capacity to provide an X-ray contrast when this is used to check the quality of the repair. Other optical effects, such as e.g. lustre of the material and the so-called opal effect, i.e. simulated translucence, can also be worth aiming at to achieve the desired aesthetics of a filling material that consists of a chemically bonded ceramic material, the binder phase of which consists mainly of a cement-based system.

ACCOUNT OF THE INVENTION

One object of the present invention is to provide a ceramic material of the type stated in the introduction, which material exhibits translucence. The material shall preferably exhibit radiopacity at the same time and also any other optical attributes that imitate the appearance of natural tooth, e.g. fluorescence, lustre and/or the opal effect.

The invention also aims to provide a powdered material that has the capacity following saturation with a liquid reacting with the binder phase to hydrate to a chemically bonded ceramic material of the type intended according to the invention.

In the following description, the term "material" is taken to mean both the powdered material and the chemically bonded ceramic material unless specifically indicated otherwise.

The term binder phase is taken to mean a cement content in the material, regardless of whether the powdered material or the hydrated ceramic product is involved.

The desired and other attributes are achieved according to the invention in that the material has a composition and/or structure suitable for giving the ceramic material translucence in the hydrated state.

According to one aspect of the invention, the binder phase is optimized for translucence of the ceramic material, preferably in terms of physical or chemical attributes of the binder phase. Alternatively, the material is optimized for translucence of the ceramic material in the form of attributes of one or more additives suitable for giving the ceramic material translucence.

According to another aspect of the invention, the ceramic material has a translucence corresponding to 35-90%, preferably 40-85% and even more preferably 50-80% opacity in the hydrated state.

According to another aspect of the invention, it is preferred that the material includes an additive that is suitable for giving the ceramic material radiopacity, while retaining or increasing the translucence of the ceramic material at the same time.

According to another aspect of the invention, the material has a composition and/or structure that is also suited to give the ceramic material other optical effects that imitate optical effects of natural tooth, which optical effects consist of any effect in the group consisting of fluorescence, lustre, opalescence, iridescence and the opal effect.

The powdered material shall further satisfy the requirements indicated above for mouldability and durability, and be easy to handle in connection with its wetting and application in a cavity, e.g. a tooth cavity. The ceramic material formed should also, for dental applications, meet the demands made on such a material according to the above. It is especially preferred that the powdered material exists in the form of a raw compact that has a compaction degree of 55-67% by volume solid phase, preferably 57-63% by volume solid phase and even more preferably 58-61% by volume solid phase prior to hydration, in a manner such as described in SE 463 493. However, the invention is also fully applicable in connection with a wet-moulded material that exists in loose powder form or in the form of granules prior to hydration, such as the powdered material described in SE 502 987. The material can also contain one or more expansion-compensating additives suitable for giving the ceramic material dimensionally stable long-term attributes, such as described in SE 514 686. It is generally the case in that connection that said binder phase consists at least chiefly of calcium aluminate cement. However, the addition of one or more other cement binder phases in a total content of less than 30% by volume can be used, preferably 1-20% by volume and even more preferably 1-10% by volume. Admixtures of ordinary Portland cement (OPC cement) or fine crystalline silica are used advantageously. Furthermore, it is desirable for the ceramic material to have a hardness of at least 50 HV in the hydrated state, preferably at least 100 HV and even more preferably 120-300 HV.

DETAILED ACCOUNT OF THE INVENTION

Different aspects that aim to achieve translucence, radiopacity, fluorescence or other optical attributes of a ceramic material of the type named in the introduction will be described below in greater detail.

Whiteness of the Binder Phase

For calcium aluminate cement the translucence can be improved by using a powder raw material for the binder phase, i.e. calcium aluminate, that has a whiteness value of over 70, preferably over 74 according to ASTM E313. In white raw materials, the absorption of light is low, which contributes to improved translucence. Transition metals in particular (in metal or oxide form) give a greyer or colored powder, which is thus undesirable. It is therefore preferred that the content of transition metals in the powder mixture is less than 0.6 percent by weight, preferably less than 0.5 percent by weight. Small quantities of oxides of transition metals can however be used to color the material to imitate natural tooth color. Iron oxides in particular can be used to this end, but in quantities below 0.5 percent by weight, preferably below 0.3 percent by weight.

Refractive Index

The refractive index in visible light of additives in the material also influences the translucence. It is preferred that the refractive index of the additives is as similar to the refractive index of the binder phase in the hydrated state as possible. To this end, additives (fillers) can be used only with the aim of improving translucence. However, it is also possible to achieve radiopacity with only a slightly impaired, retained or improved translucence by using additives that give radiopacity but have a refractive index that lies close to the refractive index of the binder phase in the hydrated state. 1.6 is stated below as the refractive index of the calcium aluminate, which is a mean value of the phases $3CaO.Al_2O_3.6H_2O$ (1.63) and $Al_2O_3.3H_2O$ (1.57), which are final phases for the hydrated binder phase. It is preferred that the refractive index of the additive does not deviate by more than 15% from the refractive index of the hydrated binder phase, preferably by not more than 10% and even more preferably by not more than 5%.

For radiopacity to be obtained, the additive shall also contain an atom type with a density of over 5 $g/cm^3$ (reckoned on the pure element), i.e. heavy metals from V and upwards in the periodic system, preferably Ba, Sr, Zr, La, Eu, Ta and/or Zn. One advantage of using an additive that contains barium and/or strontium is that since barium and strontium are in the same atomic group as calcium, barium and/or strontium can become part of the binder phase and replace calcium at certain points. In general, this is desirable, i.e. the use of additives that interact with the binder phase and/or become part of a solid solution in the same.

It is preferred that the additive is a glass, i.e. amorphous phase, most preferably a silicate glass. It is also preferred that the additive also contains fluoride.

Examples of additive materials that satisfy one or more of the stated requirements are: silicate glass, barium aluminium borosilicate glass, barium aluminium fluorosilicate glass, barium sulphate, barium fluoride, zirconium-zinc-strontium-borosilicate glass, apatite, fluorapatite and similar materials. In these materials barium can be exchanged for strontium and the materials can also contain fluoride. The additive materials can also have any morphology or form, including: spheres, regular or irregular forms, whiskers, plates or the like. Particles of the additive material should be smaller than 50 µm, preferably smaller than 20 µm and even more preferably smaller than 10 µm. The size of the particles is measured by laser diffraction and calculated as the volume mean value D[4,3].

Additive materials of this type can be present in total quantities of at least 3% by volume, preferably at least 5% by volume and even more preferably at least 10% by volume, but at most 55% by volume, preferably at most 50% by volume and even more preferably at most 45% by volume in the powdered material.

Reactive Glass

According to the "Refractive index" section, it is important, if improved translucence or at least uninterrupted translucence is to be achieved, that additives for the material, such as additives in the form of hardness-giving filler materials, match the refractive index in visible light of the material's binder phase in the hydrated state. Furthermore, if the ceramic material is to exhibit translucence and a natural appearance both in interior lighting of various types and sunlight outdoors, the refractive index of the ceramic material's binder phase and the additive material must be the same at all wavelengths within the spectrum for visible light.

According to one embodiment of the invention, this problem has been solved simply but ingeniously by the use of additives, preferably in the form of hardness-giving fillers, that are formed from the same elements as the binder phase of the powdered material. This means that the additives have the same dielectric properties, and thus the same refractive index, as the ceramic material's binder phase, at all wavelengths. According to the invention, the additive material therefore consists, like the binder phase of the powdered material, of the same type of material, suitably calcium aluminate anhydrate, the additive being present however in the glass phase. The known fact is hereby utilized that the binding agent system $CaO-Al_2O_3$ has a eutectic at 46.5% by weight CaO and 53.5% by weight $Al_2O_3$, corresponding to a principal phase of $Ca_{12}Al_{14}O_{33}$.

Calcium and aluminium raw materials are mixed therefore in a ratio close to the eutectic ratio, preferably in a ratio that gives a composition between $3CaO.Al_2O_3$ and $CaO.2Al_2O_3$, most preferably around $12 CaO.7Al_2O_3$. The mixture is heated above the eutectic temperature or more specifically above the fusion temperature for the current mixture, i.e. it is heated to over 1420° C., preferably to over 1500° C. and even more preferably to between 1500° C. and 1800° C., and then cooled quickly, e.g. in an inert liquid or against a metal sheet, a glass phase (amorphous phase) of calcium aluminate being formed. This glass phase is very transparent and can be used as an additive in the binder phase of the powdered material, this effectively increasing the translucence of the material.

A great advantage of additive material according to this embodiment of the invention is that it consists of a reactive additive material. The additive in the form of glass cement therefore has the ability following saturation with a liquid reacting with the binder phase to form a chemically bonded ceramic material. However, the additive material will hydrate more slowly than the binder phase of the powdered material, since they have different phases, which means that unreacted calcium aluminate glass will remain as a core in the additive particles and function to provide hardness. A related advantage is that the additive particles will bind better to the binder phase of the ceramic material than filler particles of another type, since at least their outer layer reacts with the hydrating liquid in the same manner as the binder phase of the powdered material, the outer layer binding to the binder phase of the powdered material. To get a less reactive additive, in which case a greater share of the same will be retained in the glass phase instead of passing over to a crystalline phase in connection with the reaction with liquid, it can be stabilized using a stabilizer, e.g. an oxide such as $SiO_2$. One advantage of a material in the glass phase compared with the crystalline phase is that the light diffusion is reduced on account of the fact that the glass grains contain a smaller quantity of light diffusion sources such as grain boundaries, due to which a positive contribution to the translucence of the ceramic material is obtained.

The glass phase can also be caused to exhibit radiopacity through the addition of elements that contain an atom type with a density above 5 g/cm$^3$ (reckoned on the pure element) according to what was stated in the section "Refractive index".

However, it should hold good, when mixing other elements/compounds (e.g. stabilizers or elements that provide radiopacity) into the additive, that these elements/compounds must have a refractive index in visible light that does not deviate by more than 15% from the refractive index of the ceramic material's hydrated binder phase, preferably by not more than 10% and even more preferably not more than 5%.

The additive material can also have any morphology or form, including: spheres, regular or irregular forms, whiskers, plates or the like. Particles of the additive material should be smaller than 50 µm, preferably smaller than 20 µm and even more preferably smaller than 10 µm. The size of the particles is measured by laser diffraction and calculated as the volume mean value D[4,3]. However, it is also conceivable to manufacture the additive material in the form of glass fibres, in a known manner, for use as an additive material according to the present invention.

The additive material can be present in total quantities of at least 3% by volume, preferably at least 5% by volume and even more preferably at least 10% by volume, but at most 55% by volume, preferably at most 50% by volume and even more preferably at most 45% by volume in the powdered material.

It is also conceivable to use a glass phase manufactured according to the above as the actual main binder phase in the powdered material. It is best not to use stabilizers in this case. However, the ceramic material formed will exhibit improved translucence even without stabilizers, since a substantial share of non-hydrated glass phase will always remain in the ceramic material. Such non-hydrated parts of material will also function as in-situ hardness-giving filler material. One possibility is also to use a stabilized glass phase as an additive in a non-stabilized main binder phase, in which case the hardness-giving effect increases.

Yet another variant of this embodiment of the invention is to use other additives in a reactive glass phase, i.e. additives in a glass phase that have the capacity following saturation with a liquid reacting with the additive to form a chemically bonded ceramic material or in other words, additives in a glass phase that participate in a weak acid base reaction or are dissolved by hydrogen ions, forming a chemically bonded ceramic material. Here it is thus conceivable to use as an additive e.g. the type of glass that is known for use in glass ionomer cement. Such glass typically contains aluminate silicate glass and is referred to below as glass ionomer glass. The principal constituents are typically $SiO_2$ and $Al_2O_3$, in all accounting for at least 40% by weight and even more preferably at least 50% by weight of the glass and roughly just as much each reckoned in moles. The glass ionomer glass also contains considerable quantities of fluoride, e.g. around 10-25% by weight or even more preferably around 15-20% by weight, which can give a positive discharge of fluoride over time, when the material in used in dental filling material. The dental filling material can thereby act to prevent decay at the same time as being translucent. The glass ionomer glass can also contain known additives such as e.g. sodium and aluminium fluorides and/or calcium or aluminium phosphates etc., each normally in amounts of 15% by weight maximum, preferably 10% by weight maximum.

In the glass ionomer cements that are known for use as dental filling material, an organic component is also included apart from the actual glass ionomer glass, normally an organic acid such as e.g. polyacrylic acid, polymaleic acid or copolymers of these. Solidification of the glass ionomer cement takes place due to cations being released from the glass ionomer glass and reacting with the acid groups in the polyacid, forming a polyalkenoate salt. Considerable quantities of aluminium are then incorporated into the matrix structure in a curing process, the physical attributes of the material being improved. According to one embodiment of the present invention, it is conceivable to mix calcium aluminate cement with glass ionomer cement, which like the cases described above, when only the actual glass ionomer glass is mixed into the calcium aluminate cement, leads to increased translucence on account of the glass and a positive discharge of fluoride over time.

Even when using additives in the form of types of reactive glass other than calcium aluminate glass, such as e.g. glass ionomer glass or glass ionomer cement containing glass ionomer glass, it should however hold good that the refractive index of the additive should not deviate too much from the refractive index of the ceramic material, according to the above. The content of the additive should not exceed 25% by volume, even more preferably should be less than 15% by volume and still more preferably less than 10% by volume. Other aspects also according to the above should apply where applicable, e.g. the use of additives providing radiopacity. The same type of advantages are also achieved, also with regard to the hardness-giving function of the glass phase, thanks to incomplete reaction with the liquid phase.

Porosity

The translucence can be improved by a low level of porosity in the finished ceramic material, preferably a porosity level of less than 20%, even more preferably of less than 10% and still more preferably less than 5%. This also is due to the phenomenon concerned with the refractive index. In the mouth, the pores are filled with saliva/water, which has a refractive index of 1.33. Thus—the lower the porosity, the less the quantity of saliva/water that deviates in the refractive index in comparison with the binder phase. The size of the pores should be less than 5 µm, preferably less than 1 µm and still more preferably less than 300 nm.

The porosity can be influenced by grinding of the powdered binder phase and checking the mechanical pressure in the production of the hydrated material. During production of raw compacts, the mechanical pressure for example should be preferably 40-300 MPa and even more preferably 70-250 MPa and the degree of compaction that is achieved thereby should be in accordance with what was indicated above for raw compacts. In production in the form of suspension of dissolved powdered material in the liquid reagent, preliminary draining is preferably executed at a pressure below 10 MPa, to a degree of compaction of 35-50% by volume solid phase. Final compaction then takes place at a pressure of at least 20 MPa, preferably at least 30 MPa, even more preferably at least 50 MPa and up to 300 MPa, to a final degree of compaction of 47-70% by volume solid phase, preferably >51% by volume solid phase and even more preferably >55% by volume solid phase. During production from a granulated powder material, compression is carried out at a pressure of preferably 40-300 MPa, even more preferably 70-250 MPa, to a final degree of compaction of 47-70% by volume solid phase, preferably >51% by volume solid phase and even more preferably >55% by volume solid phase.

Particle Size

The particle size of the phases included in the material, especially of the binder phase, is significant since the light is diffused in the grain boundaries. The particle size should therefore be optimized with regard to strength and light diffusion. It is preferred to have particle sizes of less than 80 µm, preferably less than 20 µm and still more preferably less than 15 µm. The particle size is measured by laser diffraction and a unit-weighted mean value is given (also called D[4, 3]).

The translucence can also be improved further if the amount of particles of the same magnitude as the wavelength of visible light, i.e. 300-800 nm, is minimized. It is preferred here to have particle sizes in the material of over 3 µm, preferably over 2 µm and even more preferably over 1 µm and/or particle sizes under 300 nm, preferably under 200 nm. This can be achieved for example by screening of the powdered binder phase. Screening can be carried out by means of a number of different techniques that are known in themselves, e.g. air stream separation or wet screening with cloth.

Phase Composition

To control the composition of the binder phase, the number of phases in the final product can be minimized, which results in reduced opacity. This is due to the fact that the refraction decreases, since the difference in refractive index between grains of the same phase is zero. A mixture of the phases $3CaO.Al_2O_3$ and $CaO.2Al_2O_3$ is particularly preferred in the powdered material with a simultaneous minimization of $CaO.2Al_2O_3$. This means that the amount of $Al_2O_3.3H_2O$ in the final product can be minimized or omitted completely, only $3CaO.Al_2O_3.6H_2O$ being formed by the binder phase instead. According to one aspect of the invention, the binder phase of the powdered material consists up to at least 70% by weight, preferably at least 80% by weight and even more preferably at least 90% by weight, of $CaO.Al_2O_3$ and/or $3CaO.Al_2O_3$.

By only using $CaO.Al_2O_3$ and/or $3CaO.Al_2O_3$ on the whole as the binder phase in this way, the hydrated material can be guided to contain $Al_2O_3.3H_2O$ to $3CaO.Al_2O_3.6H_2O$ in a ratio of 2:1 maximum, preferably less than 1:5 and even more preferably less than 1:10.

Surface

The surface of the ceramic material, in the hydrated state and following any post-treatment of the material, can also affect the translucence. The surface preferably has a surface roughness, measured as $R_a$, that is less than 10 μm, preferably less than 2 μm and even more preferably less than 1 μm. This can be achieved by grinding/polishing of the surface with sufficiently fine grinding/polishing agents or grinding/polishing tools.

Additives that Provide Lustre

Stratified ceramic material, i.e. material with a given cleavage surface, e.g. mica and feldspar, can be used as additives to give the material lustre and mechanical strength. The use of fluormica is particularly preferred, since it is a beneficial source of fluoride for the teeth. At least 1% by volume, preferably at least 5% by volume but at most 20% by volume, preferably at most 15% by volume of stratified material is best used in the powdered material. Mechanical strength can also be attained by means of a stratified ceramic material of this kind thanks to its lamellar structure, which means that it acts like a reinforcing material. The particles should be smaller than 50 μm, preferably smaller than 20 μm and even more preferably smaller than 10 μm.

Fluorescent Additives

To achieve fluorescence, fluorescent additives are best used, in particular substances that contain ions of rare earths: Ce, Pr, Nd, Pm, Sm, Eu, Gd, Tb and Dy. Additives that contain Eu ions are particularly preferred, as they give a fluorescence that resembles that of the natural tooth. According to another aspect, it is preferred to have fluorescent additives that contain F-ions. Examples of preferred fluorescent additives are fluorapatites with dissolved lanthanide and oxides of lanthanides.

Additive materials of this type can be present in total quantities of at least 0.1% by volume, preferably at least 0.5% by volume and even more preferably at least 1% by volume, but at most 15% by volume, preferably at most 10% by volume and even more preferably at most 8% by volume in the powdered material.

The Opal Effect

The opal effect, meaning the impression of translucence, can be achieved by using orange and blue color tones in the material or on the surface of the finished ceramic material.

EXAMPLE 1

A series of experiments was carried out to study the effect of different translucence- or radiopacity-promoting additives on light opacity and radiopacity of the hydrated ceramic material.

Description of Raw Materials

Calcium aluminate of the phases $CaO.Al_2O_3$ and $CaO.2Al_2O_3$ forming part of e.g. Ca-aluminate cement (Alcoa or alternatively Lafarge) $BaF_2$, $BaSO_4$ (Merk), $Al_2O_3$ (Baikalox), $SnO_2$ (Aldrich), dental glass (Schottsvenska), silicate glass (Schottsvenska).

Experiments a)-j) Below Describe:
a) Opacity of the hydrated calcium aluminate, without action or additives, but with filler providing radiopacity (reference).
b) Effect of removing filler on a)
c) Effect of filler providing radiopacity on b), $BaSO_4$
d) Effect of filler providing radiopacity on b), $BaF_2$
e) Effect of filler providing radiopacity on b), $BaO—SiO_2—B_2O_3—Al_2O_3$ glass
f) Effect of filler providing radiopacity on b), $BaO—F—SiO_2—B_2O_3—Al_2O_3$ glass
g) Effect of filler providing radiopacity on b), $SiO_2—B_2O_3—Al_2O_3—F—SrO—Na_2O—CaO—ZnO—La_2O_3—ZrO_2$ glass
h) Effect of filler providing hardness on b), $Al_2O_3$
i) Effect of opacity-reducing filler on b), silicate glass
j) Effect of combination of various additives on b)

Calcium aluminates, $CaO.Al_2O_3$ and $CaO.2Al_2O_3$ with the mol ratio 1:1 are mixed with filler particles and secondary additives (all content information in relation to the calcium aluminate content) as below.
a) Addition of filler, 15% by volume $SnO_2$ (refractive index 2)
b) No addition of filler
c) Addition of 15% by volume $BaSO_4$ (refractive index 1.6)
d) Addition of 15% by volume $BaF_2$ (refractive index 1.48)
e) Addition of 40% by volume glass with composition 30% by weight BaO—50% by weight $SiO_2$—10% by weight $B_2O_3$—10% by weight $Al_2O_3$ (refractive index 1.55)
f) Addition of 40% by volume glass with composition 30% by weight BaO—1% by weight F—49% by weight $SiO_2$—10% by weight $B_2O_3$—10% by weight $Al_2O_3$ (refractive index 1.55)
g) Addition of 40% by volume glass with composition 30% by weight $SiO_2$—5% by weight $B_2O_3$—5% by weight $Al_2O_3$—2% by weight F—25% by weight SrO—5% by weight $Na_2O$—5% by weight CaO—10% by weight ZnO—5% by weight $La_2O_3$—10% by weight $ZrO_2$ (refractive index 1.606)
h) Addition of 40% by volume $Al_2O_3$ (refractive index 1.76)
i) Addition of 40% by volume silicate glass (refractive index 1.46)
j) Addition of secondary phases in the form of 10% by volume silicate glass and 30% by volume $BaO—SiO_2$-glass.

The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to measurements of translucence/light opacity or radiopacity. The measurements of opacity were carried out according to ISO 9917 (100% means opaque and 35% to 90% means translucence) and the measurements of radiopacity according to the ANSI/ADA Specification No. 27 (1 mm test body as opaque as 2 mm Al). The results are shown in Table 1.

TABLE 1

| Sample designation | Opacity (%) ($C_{0.70}$) | Radiopacity |
|---|---|---|
| A | 100 | Yes |
| B | 73 | No |
| C | 75 | Yes |

TABLE 1-continued

| Sample designation | Opacity (%) ($C_{0.70}$) | Radiopacity |
|---|---|---|
| D | 77 | Yes |
| E | 65 | Yes |
| F | 65 | Yes |
| G | 55 | Yes |
| H | 73 | No |
| I | 63 | No |
| J | 63 | Yes |

From the results it is evident that a translucent and radiopaque product can be produced. Furthermore, it is evident that the refractive index for the additive material is crucial for being able to obtain both radiopacity and translucence at the same time.

EXAMPLE 2

Experiments were carried out to study the effect of grain size of the calcium aluminate and porosity of the hydrated material on the opacity of the hydrated material.

Description of Raw Materials

Calcium aluminate of the phases $CaO.Al_2O_3$ and $CaO.2Al_2O_3$ forming part of e.g. Ca-aluminate cement (Alcoa or alternatively LaFarge).

Examples a)-g) Below Describe:
a) Opacity of the calcium aluminate in hydrated aluminate (reference).
b) Effect of reduced mean grain size of calcium aluminate on a)
c) Effect of reduced mean grain size of calcium aluminate compared with b) on a)
d) Effect of screening of c on a)
e) Effect of reduced porosity of the ready-hydrated material on a)
f) Effect of increased porosity of the ready-hydrated material on a)
g) Effect of d) and e) on a)

Calcium aluminates, $CaO.Al_2O_3$ and $CaO.2Al_2O_3$, with a mol ratio 1:1 were used in the examples.

The materials are ground in a ball mill with inert grinding balls of silicon nitride with a filling level of 35%. Isopropanol is used as the grinding liquid. To vary the grain size of the calcium aluminate, the grinding time was varied. The grain size was measured by laser diffraction and determined weighted against the volume mean value D[4,3]. The porosity of the hydrated material was varied by using different mechanical pressure in the production of the sample bodies. The porosity was measured by means of scanning electron microscope and image analysis. Following evaporation of the solvent, cylindrical raw compacts were made with a diameter of 10 mm and a height of 1 mm, which were wetted with water. The material was then kept moist at 37° C. for a week prior to measurements of opacity. The measurements of opacity were carried out according to ISO 9917.

The following action was taken in the examples:
a) The calcium aluminate was ground to a grain size distribution with all grains under 40 micrometres. The porosity was controlled to 10% in the ready-hydrated material by controlling the mechanical pressure in production of the hydrated material.
b) The calcium aluminate was ground to a grain size distribution with all grains under 20 micrometres. The porosity was controlled to 10% in the ready-hydrated material by controlling the mechanical pressure in production of the hydrated material.
c) The calcium aluminate was ground to a grain size distribution with all grains under 10 micrometres. The porosity was controlled to 10% in the ready-hydrated material by controlling the mechanical pressure in production of the hydrated material.
d) The calcium aluminate was ground to a grain size distribution with all grains under 10 micrometres. Following grinding, most of the grains below 3 micrometres were removed by air stream separation. Following screening, 90% of the grains were found to be between 3 and 10 micrometres. The porosity was controlled to 10% in the ready-hydrated material by controlling the mechanical pressure in production of the hydrated material.
e) The calcium aluminate was ground to a grain size distribution with all grains under 40 micrometres. The porosity was controlled to 5% in the ready-hydrated material by controlling the mechanical pressure in production of the hydrated material.
f) The calcium aluminate was ground to a grain size distribution with all grains under 40 micrometres. The porosity was controlled to 20% in the ready-hydrated material by controlling the mechanical pressure in production of the hydrated material.
g) The calcium aluminate was ground to a grain size distribution with all grains under 10 micrometres. Following grinding, most of the grains below 3 micrometres were removed by screening. Following screening, 90% of the grains were found to be between 3 and 10 micrometres. The porosity was controlled to 5% in the ready-hydrated material by controlling the mechanical pressure in production of the hydrated material.

The results are shown in Table 2.

| Sample designation | Opacity (%) ($C_{0.70}$) |
|---|---|
| A | 74 |
| B | 70 |
| C | 86 |
| D | 64 |
| E | 66 |
| F | 96 |
| G | 60 |

The result shows that a low porosity and a narrow grain size distribution are advantageous for achieving a lower opacity.

EXAMPLE 3

Experiments were carried out to study the effect of the surface roughness on the opacity of the material.

Description of Raw Materials

Calcium aluminate of the phases $CaO.Al_2O_3$ and $CaO.2Al_2O_3$ forming part of e.g. Ca-aluminate cement (Alcoa or alternatively LaFarge).

Description of Grinding and Polishing

To produce surfaces of varying roughness, the hydrated material was ground using abrasive paper from 80 mesh (SiC) down to 1 micrometre diamond particles on cloth. Prior to measurement of the translucence, the roughness of the surface was measured ($R_a$ value) by means of a drag needle (Alpha-step, Tencor Instruments).

Examples a)-e) Below Describe
a) The translucence of the calcium aluminate in hydrated aluminate, coarsely ground with 80 mesh SiC paper.
b) Effect of grinding with 320 mesh SiC paper on a)
c) Effect of grinding with 500 mesh SiC paper on a)
d) Effect of grinding with 1200 mesh SiC paper on a)
e) Effect of polishing using diamond paste (one micrometre diamond grain) on a)

Calcium aluminates, $CaO.Al_2O_3$ and $CaO.2Al_2O_3$, with a mol ratio 1:1 were used in the example.

The materials are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The hydrated sample bodies were then ground with abrasive paper according to the test schedule. The material was then kept moist at 37° C. for a week prior to measurements of opacity. The measurements of opacity were carried out according to ISO 9917. The results are shown in Table 3.

TABLE 3

| Sample designation | Opacity (%) ($C_{0.70}$) | $R_a$ (μm) |
|---|---|---|
| A | 100 | 15 |
| B | 76 | 2 |
| C | 71 | 0.5 |
| D | 67 | 0.1 |
| E | 63 | 0.04 |

The results show that a translucent product can be obtained by controlling the roughness of the surface.

EXAMPLE 4

Experiments were carried out to study the effect of the composition of the binder phase on the opacity of the hydrated material.

Description of Raw Materials
Calcium aluminate of the phases $CaO.Al_2O_3$ and $CaO.2Al_2O_3$ and $3CaO.Al_2O_3$.

Experiments a)-d) Below Describe:
a) Opacity of hydrated calcium aluminate, hydrated from a powder mix with the mol ratio $CaO.Al_2O_3$: $CaO.2Al_2O_3$=1:1 (reference)
b) Opacity of hydrated calcium aluminate, hydrated from a powder mix consisting of $CaO.Al_2O_3$
c) Opacity of hydrated calcium aluminate, hydrated from a powder mix with the mol ratio $3CaO.Al_2O_3$: $CaO.Al_2O_3$=1:1
d) Opacity of hydrated calcium aluminate, hydrated from a powder mix consisting of $3CaO.Al_2O_3$ The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The mixtures were then kept moist at 37° C. for a week prior to measurements of opacity. The measurements of opacity were carried out according to ISO 9917. The results are shown in Table 4.

TABLE 4

| Sample designation | Opacity (%) ($C_{0.70}$) |
|---|---|
| A | 74 |
| B | 60 |
| C | 55 |
| D | 40 |

From the results it is evident that a translucent product can be produced. Furthermore, it is evident that the opacity can be reduced by the choice of phase composition in the binder phase.

EXAMPLE 5

Experiments were carried out to study the effect of mica on the lustre of the material.

Description of Raw Materials
Calcium aluminate of the phases $CaO.Al_2O_3$ and $CaO.2Al_2O_3$ forming part of e.g. Ca-aluminate cement (Alcoa or alternatively LaFarge), mica (Chemiemineralien).

Examples a)-e) Below Describe
a) The brightness of the calcium aluminate in hydrated aluminate, without action or additives.
b) The effect of adding mica on a).

Calcium aluminates, $CaO.Al_2O_3$ and $CaO.2Al_2O_3$, with a mol ratio 1:1 are mixed with secondary additives (all content information in relation to the content of calcium aluminate) as set out below.
a) No addition
b) Addition of 10% by volume of mica.

The materials are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to visual verification of the appearance.

The results show visually that a greater lustre is obtained in the material.

EXAMPLE 6

Experiments were carried out to study the effect on fluorescence of the material of various fluorescence-promoting additives.

Description of Raw Materials
Calcium aluminate of the phases $CaO.Al_2O_3$ and $CaO.2Al_2O_3$ forming part of e.g. Ca-aluminate cement (Alcoa or alternatively LaFarge), $CaF_2$ (Aldrich), fluorapatite with lanthanide dissolved in, oxide of lanthanide.

Examples a)-e) Below Describe
a) The fluorescence of calcium aluminate in hydrated aluminate (reference).
b) Effect of secondary phase on a), $CaF_2$
c) Effect of secondary phase on a), fluorapatite with dissolved lanthanide (Eu)
d) Effect of secondary phase on a), oxide of lanthanide
e) Effect of combination of various additives on a)

Calcium aluminates, $CaO.Al_2O_3$ and $CaO.2Al_2O_3$, with the mol ratio 1:1 are mixed with filler particles and secondary additives (all content information in relation to the calcium aluminate content) as set out below.

a) No addition of filler
b) Addition of 5% by volume $CaF_2$
c) Addition of 5% by volume fluorapatite with dissolved Eu
d) Addition of 5% by volume cerium oxide
e) Addition of 3% by volume $CaF_2$ and 3% by volume fluorapatite with dissolved Eu The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to measurements of fluorescence. The measurements of fluorescence were carried out on a spectrophotometer (Minolta). The results are shown in Table 5.

TABLE 5

| Sample designation | Fluorescence, excited using UV light $\lambda < 400$ nm |
| --- | --- |
| A | No |
| B | Yes, blue |
| C | Yes, blue |
| D | Yes, blue-green |
| E | Yes, blue |

The results show that a fluorescent product can be obtained by adding fluorescent substances.

EXAMPLE 7

Experiments were carried out to study the effect of different whiteness of the raw materials on the opacity of the material.

The raw materials used were calcium aluminate of the phases $CaO.Al_2O_3$ and $CaO.2Al_2O_3$ forming part of e.g. Ca-aluminate cement (Alcoa or alternatively LaFarge).

Experiments a)-b) describe the effect of whiteness (according to ASTM E313) of the raw materials on opacity for the hydrated material.
a) Calcium aluminate with a whiteness of 60
b) Calcium aluminate with a whiteness of 72

The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to measurements of opacity. The measurements of opacity were carried out according to ISO 9917 (100% signifies opaque and 35% to 90% translucence). The results are shown in Table 6.

TABLE 6

| Sample designation | Opacity (%) ($C_{0.70}$) |
| --- | --- |
| A | 98 |
| B | 73 |

The results show that the whiteness of the raw materials has an effect on the opacity of the material such that a whiter raw material produces lower opacity.

EXAMPLE 8

A series of experiments was carried out to study the effect of admixtures of glass of calcium aluminate on light opacity and radiopacity.

Description of Raw Materials
Calcium aluminate ($CaO.Al_2O_3$) and glass with the composition $12CaO.7Al_2O_3$ and dental glass (Schott).

Experiments a)-d) Below Describe:
k) Light opacity of $CaO.Al_2O_3$ without additives
l) Effect of addition of $12CaO.7Al_2O_3$-glass on a)
m) Effect of filler providing radiopacity (non-reactive dental glass) on b)
n) Effect of using only glass phases on a), i.e. both in the main binder phase and in filler providing radiopacity.

Calcium aluminate, $CaO.Al_2O_3$ is mixed with filler particles in experiments a)-c).
k) No addition
l) Addition of 30% by volume $12CaO.7Al_2O_3$-glass
m) Addition of 40% by volume dental glass with the composition 30% by weight $SiO_2$—5% by weight $B_2O_3$—5% by weight $Al_2O_3$—2% by weight F—25% by weight SrO—5% by weight $Na_2O$—5% by weight CaO—10% by weight ZnO—5% by weight $La_2O_3$—10% by weight $ZrO_2$ (refractive index 1.606) to b)
n) Mixture of 60% $12CaO.7Al_2O_3$-glass and 40% dental glass with the composition 30% by weight $SiO_2$—5% by weight $B_2O_3$—5% by weight $Al_2O_3$—2% by weight F—25% by weight SrO—5% by weight $Na_2O$—5% by weight CaO—10% by weight ZnO—5% by weight $La_2O_3$—10% by weight $ZrO_2$ (refractive index 1.606).

The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to measurements of translucence/light opacity or radiopacity. The measurements of opacity were carried out according to ISO 9917 (100% signifies opaque and 35% to 90% translucence) and measurements of radiopacity according to ANSI/ADA Specification No. 27 (1 mm sample body as opaque as 2 mm Al). The results are shown in Table 7.

TABLE 7

| Sample designation | Opacity (%) ($C_{0.70}$) | Radiopacity |
| --- | --- | --- |
| A | 65 | No |
| B | 51 | No |
| C | 56 | Yes |
| D | 47 | Yes |

It is evident from the results that a translucent and radiopaque product can be produced and that the light opacity decreases if all or a part of the binder phase is exchanged for a glass phase of calcium aluminate.

EXAMPLE 9

A series of experiments was carried out to study the effect of admixtures of reactive glass on light opacity.

Description of Raw Materials
Calcium aluminate ($12CaO.7Al_2O_3$) and reactive glass containing fluoride (Schott) and calcium aluminate glass.

Experiments a)-d) Below Describe:
a) Light opacity of crystalline $12CaO.7Al_2O_3$ without additives
b) Effect of addition of $12CaO.7Al_2O_3$-glass on a)
c) Effect of addition of $CaO.Al_2O_3$-glass on a)
d) Effect of using only $12CaO.7Al_2O_3$-glass
e) Effect of using reactive glass ionomer glass containing fluoride on a)

Calcium aluminate, $12CaO.7Al_2O_3$ is mixed with filler particles in experiments a)-c) and e).
a) No addition
b) Addition of 30% by volume $12CaO.7Al_2O_3$-glass to a)
c) Addition of 30% by volume $CaO.Al_2O_3$-glass to a)
d) Crystalline $12CaO.7Al_2O_3$ is left out and only $12CaO.7Al_2O_3$-glass is used.
e) Addition of 10% by volume glass of the composition: 30% by weight $SiO_2$—20% by weight $SrO$—20% by weight $Al_2O_3$—15% by weight F—10% by weight ZnO and remaining $P_2O_5$ and $Na_2O$ to a).

The mixtures are ground in a ball mill with inert grinding balls of silicon nitride with a filling level of 35%. Isopropanol is used as the grinding liquid. Following evaporation of the solvent, cylindrical raw compacts were made with a diameter of 10 mm and a height of 1 mm, which were wetted with water. The material was then kept moist at 37° C. for a week prior to measurements of translucence/light opacity or radiopacity. The measurements of opacity were carried out according to ISO 9917 (100% signifies opaque and 35% to 90% translucence). The results are shown in Table 8.

TABLE 8

| Sample designation | Opacity (%) ($C_{0.70}$) |
|---|---|
| A | 62 |
| B | 50 |
| C | 53 |
| D | 45 |
| E | 58 |

It is evident from the results that a translucent and radiopaque product can be produced and that the light opacity decreases if all or a part of the binder phase is exchanged for a glass phase that participates in acid-base reactions.

The invention is not restricted to the embodiments detailed but can be varied within the scope of the claims.

The invention claimed is:

1. Powdered material, the binder phase of which mainly comprises a cement-based system, which powdered material has the capacity following saturation with a liquid reacting with the binder phase to hydrate to a chemically bonded ceramic material, suitable for dental purposes, wherein the binder phase comprises at least mainly of calcium aluminate cement and that it further comprises one or more glass additives that have a refractive index in visible light that deviates by 15% at most from the refractive index of the binder phase when the binder phase is hydrated, a majority of particles have a size greater than 1 µm and less than 80 µm and/or less than 300 nm, the whiteness value of the binder phase being greater than 70 according to ASTM E313, the powdered material giving the chemically bonded ceramic material translucence in the hydrated state, and wherein the glass additives are present at 10-45% by volume.

2. The powdered material according to claim 1, wherein the powdered material forms a raw compact that has a degree of compaction of 55-67% by volume solid phase.

3. The powdered material according to claim 1, wherein the powdered material is present in loose powder form or in the form of granules.

4. The powdered material according to claim 1, wherein the binder phase mainly comprises $3CaO.Al_2O_3$ and/or $CaO.Al_2O_3$.

5. The powdered material according to claim 1, wherein said additive comprises a glass phase that following saturation with the liquid reacting with the binder phase hydrates to a chemically bonded ceramic material.

6. The powdered material according to claim 1, wherein the binder phase comprises calcium aluminate in the state of a glass.

7. The powdered material according to claim 1, wherein the additives have a refractive index in visible light that deviates by 10% at most from the refractive index of the binder phase when the binder phase is hydrated.

8. The powdered material according to claim 1, wherein the additives have a refractive index in visible light that deviates by 5% at most from the refractive index of the binder phase when the binder phase is hydrated.

9. The powdered material according to claim 1, wherein said additive consists of particles of silicate glass.

10. The powdered material according to claim 1, wherein said additive is also suitable for giving the ceramic material radiopacity, said additive containing an atom type with a density above 5 g/cm³.

11. The powdered material according to claim 10, wherein said atom is Zr, La, Ta, Zn, Ba and/or Sr, and/or which additive also contains fluoride.

12. The powdered material according to claim 5, wherein said additive in the grass phase comprises glass ionomer glass in a content less than 25% by volume.

13. The powdered material according to claim 1, wherein it contains one or more additives that give the ceramic material lustre, said additives comprising a stratified ceramic material and/or blue and orange coloring agents that give the ceramic material opal effect.

14. The powdered material according to claim 13, wherein said stratified ceramic material is mica or feldspar.

15. Chemically bonded ceramic material comprising the powered material according to one of claims 1-14 in hydrated form, wherein the hydrated material is translucent.

16. The chemically bonded ceramic material according to claim 15, wherein it has a hardness of at least 50 HV.

17. The chemically bonded ceramic material according to claim 15, wherein it has a porosity of less than 20%.

18. The chemically bonded ceramic material according to claim 15, wherein it has a surface, which surface gives the material translucence, said surface having a surface roughness, measured as $R_a$, lower than 10 µm.

* * * * *